(12) United States Patent
Caillouette

(10) Patent No.: US 7,458,941 B2
(45) Date of Patent: Dec. 2, 2008

(54) MULTI-PURPOSE VAGINAL MOISTURE SCREENING

(75) Inventor: James C. Caillouette, Pasadena, CA (US)

(73) Assignee: FemTek LLC, Pasadena, CA (US)

(*) Notice: Subject to any disclaimer, the term of this patent is extended or adjusted under 35 U.S.C. 154(b) by 0 days.

(21) Appl. No.: 11/354,656

(22) Filed: Feb. 16, 2006

(65) Prior Publication Data

US 2007/0073192 A1    Mar. 29, 2007

Related U.S. Application Data

(63) Continuation-in-part of application No. 11/235,741, filed on Sep. 26, 2005.

(51) Int. Cl.
- *A61B 10/00* (2006.01)
- *A61B 5/00* (2006.01)
- *B65D 81/00* (2006.01)

(52) U.S. Cl. .................................. 600/572; 600/585

(58) Field of Classification Search ................ 600/572, 600/573, 582, 584
See application file for complete search history.

(56) References Cited

U.S. PATENT DOCUMENTS

| | | | |
|---|---|---|---|
| 4,643,980 A * | 2/1987 | Witonsky et al. ............ 436/128 |
| 5,710,372 A * | 1/1998 | Becket ..................... 73/53.01 |
| 5,762,614 A | 6/1998 | Caillouette |
| 5,782,801 A | 7/1998 | Caillouette |
| 5,827,200 A | 10/1998 | Caillouette |
| 5,916,176 A | 6/1999 | Caillouette |
| 6,013,036 A | 1/2000 | Caillouette |
| 6,019,734 A * | 2/2000 | Parkinson ................. 600/572 |
| 6,117,090 A | 9/2000 | Caillouette |
| 6,390,991 B1 | 5/2002 | Caillouette |
| 6,406,441 B1 | 6/2002 | Caillouette |
| 6,544,196 B2 | 4/2003 | Caillouette |

* cited by examiner

*Primary Examiner*—Max Hindenburg
*Assistant Examiner*—Jonathan M Foreman
(74) *Attorney, Agent, or Firm*—William W. Haefliger

(57) ABSTRACT

The method of quickly screening for vaginal moisture conditions, that includes providing a manually manipulable element including a probe insertible into the vagina; providing one or more pH indicating first test site or sites on one portion of the probe; providing a vaginosis test site on another portion of the probe; manipulating the probe to transfer vaginal moisture to the sites, and, therefore, externally of the vagina, applying an hydroxide to the vaginosis test site, to come in contact with moisture at the vaginosis test site; and detecting presences of an amine or amines produced at the vaginosis site.

15 Claims, 7 Drawing Sheets

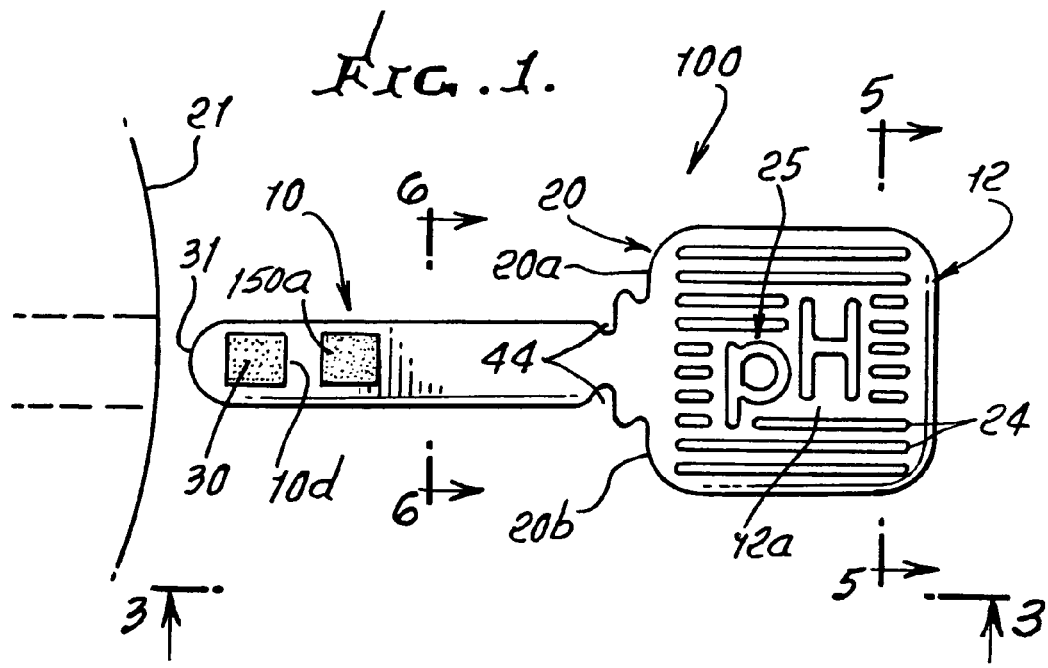
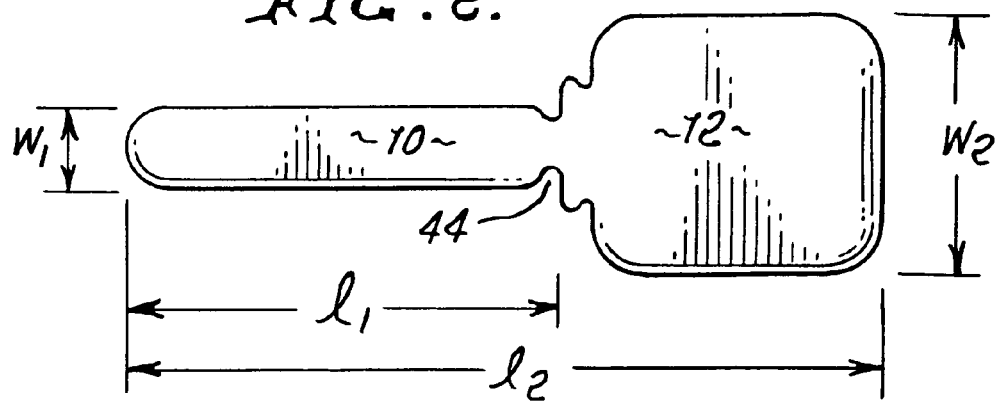
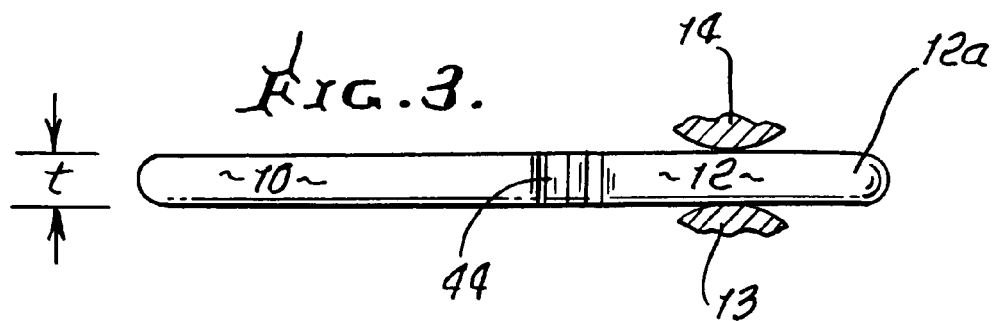

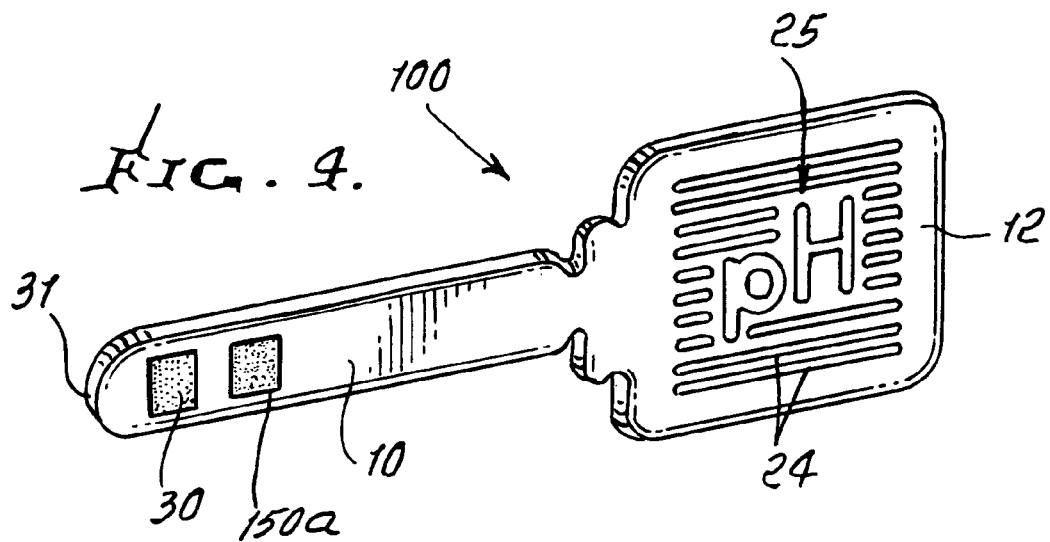
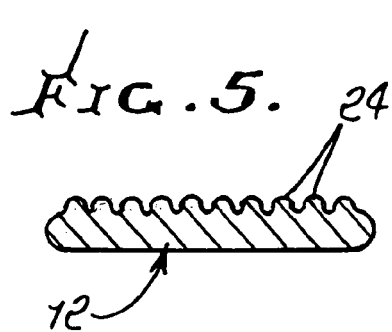
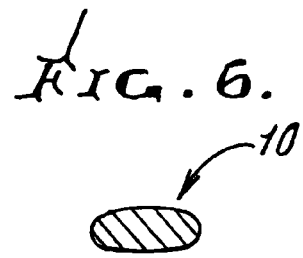
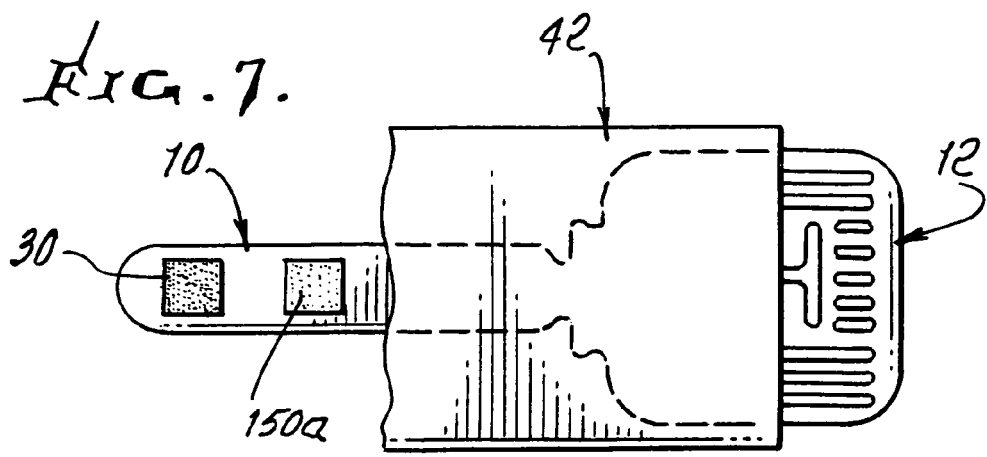

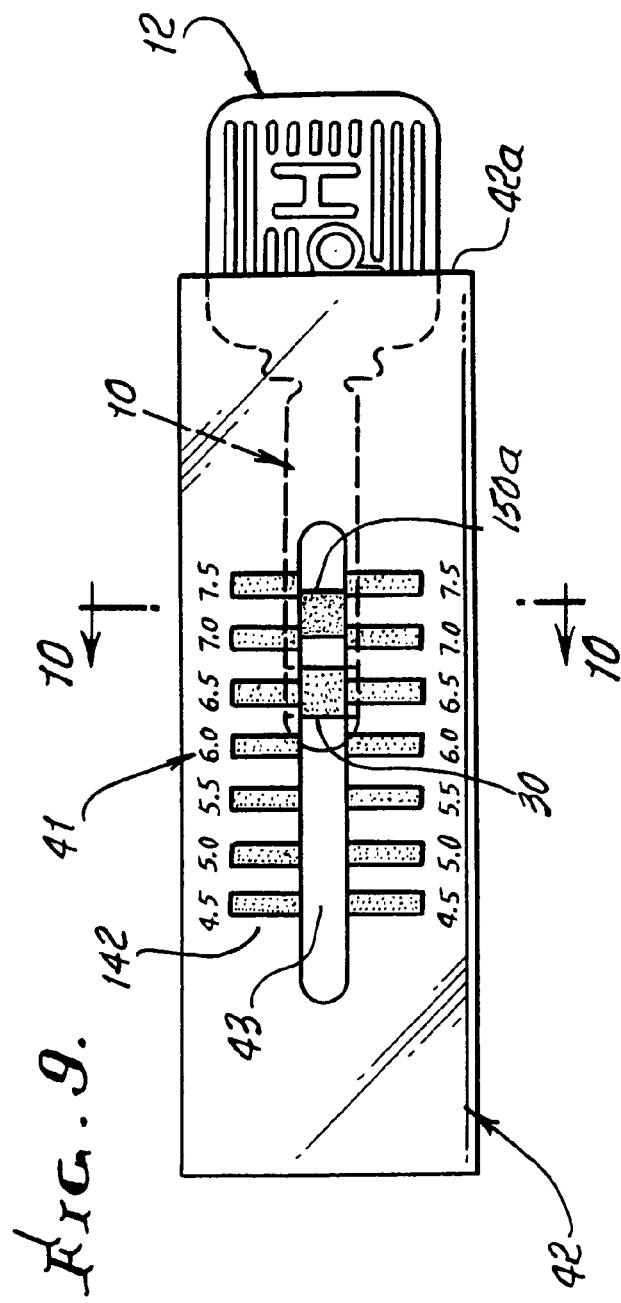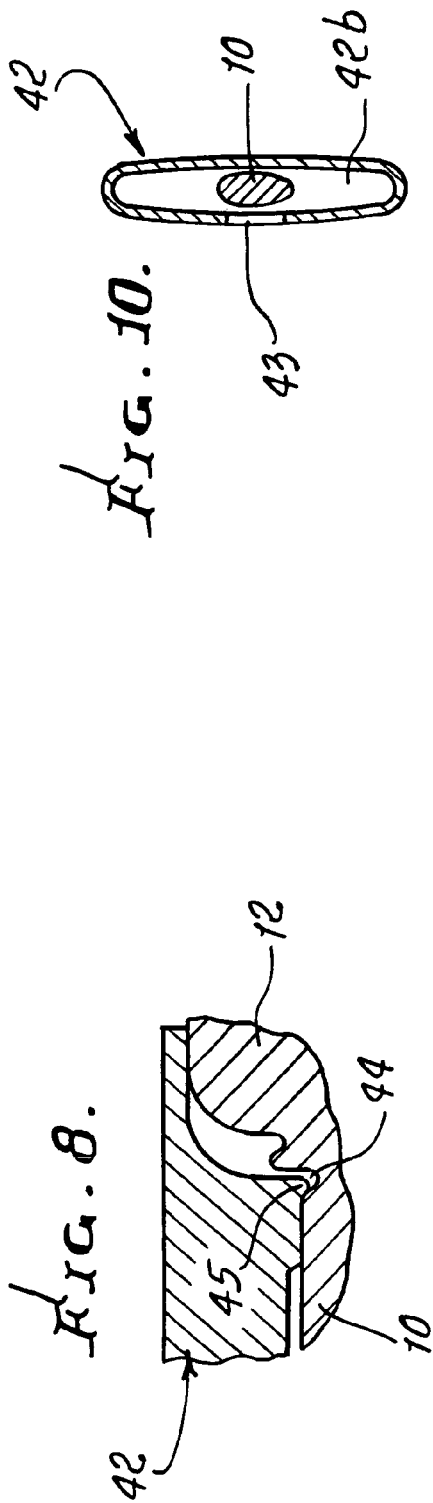

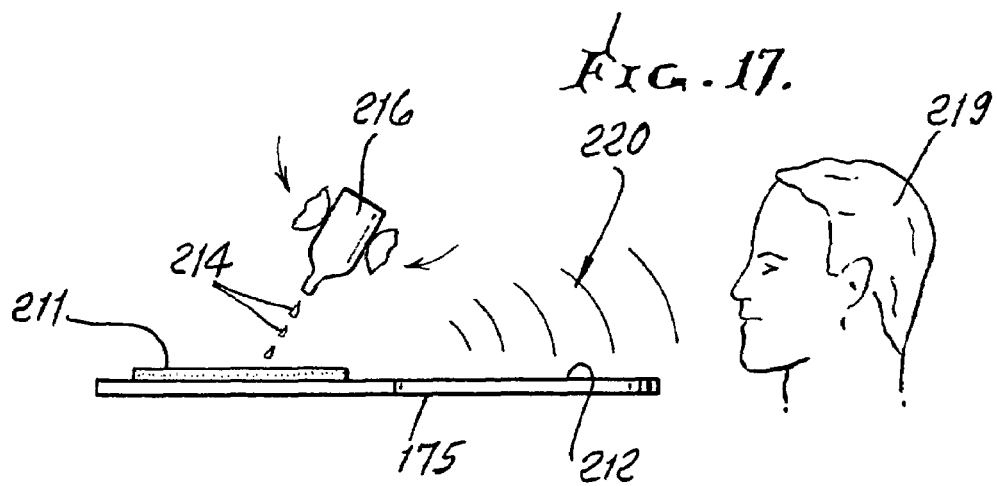
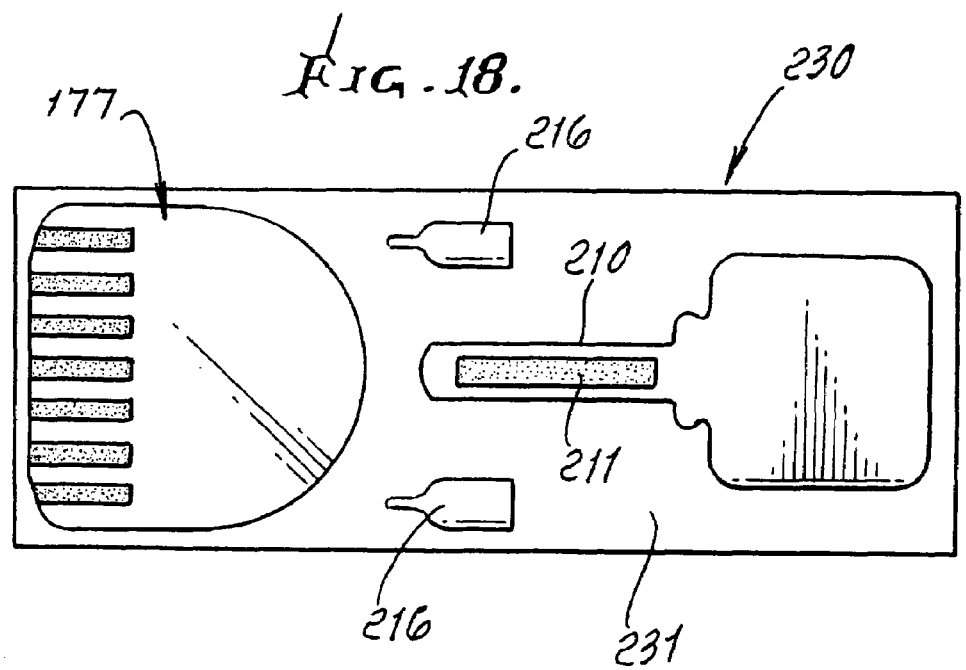

MULTI-PURPOSE VAGINAL MOISTURE SCREENING

This application is a continuation-in-part of prior U.S. patent application Ser. No. 11/235,741, filed Sep. 26, 2005.

BACKGROUND OF THE INVENTION

This invention relates generally to testing of body fluid, one example being pH measurement of body fluid, such as vaginal and/or urethral fluid, or moisture, and more particularly, to a rapid, easily performed method of such testing, or obtaining such measurement, as on a preliminary rapid basis. Also, it relates to multiple purpose screening of vaginal moisture.

There is continued need to obtain pH measurement of vaginal fluid, as for example in the determination of whether amniotic fluid has escaped into the vagina, during late pregnancy; another example is testing to determine need for estrogen therapy. There is also need for quick, simple test determination that positively alerts the user to possible problems indicated by changed conditions in the vagina as for example amine presence in vaginal moisture.

SUMMARY OF THE INVENTION

It is a major object of the invention to provide an improved vaginal probe apparatus and quick test procedure which meets the above needs. Basically, the screening method of the invention includes:

a) providing a manually manipulable element including a probe insertible into the vagina, b) providing one or more pH indicating first test site or sites on one portion of the probe, c) providing a vaginosis test site on another portion of the probe, d) manipulating the probe to transfer vaginal moisture to said sites, e) and, therefore, externally of the vagina, applying an hydroxide to the vaginosis test site, to come in contact with moisture at said vaginosis test site, f) and detecting presence of an amine or amines produced at said vaginosis site.

Additional steps include:

g) withdrawing the probe from the vagina between said steps d) and e), and h) observing the coloration of said pH indication site as an indication of pH level.

As will be seen, the probe typically has opposite sides, said one portion of the probe located at one of said sides, and said other portion of the probe located at another of said opposite sides.

Another object includes the provision of a carrier for said hydroxide, and manipulating said carrier to effect said application of the hydroxide to the vaginosis test site after said moisture transfer thereto. The carrier may in this regard be provided in the form of an easily manipulated ampule, which may be initially located on a support for the probe, the assembly being in kit form.

A further object includes provision of the vaginosis test site in elongated form at one side of the probe, that site typically consisting of an absorbent material, examples being "waste lock" from M2 polymer, or highly absorbent "Lyocell Fiber" disclosed in "Medical Textiles", June 2003, page 3.

Test sites on the probe are preferably located at opposite sides of the probe, as for example in opposition to one another, enabling maximum site area for exposure to moisture, enhancing use efficiency as by a "whiff test" for amine.

An additional object includes selection of the hydroxide from the group:
 i) KOH,
 ii) milk of magnesia,
 iii) sea water,
 iv) baking soda, or mixture thereof with water.

Yet another object includes provision of the pH test, to include
 i) a pH indicator characterized as producing a color which corresponds to pH level of vaginal moisture contacting the indicator,
 ii) a local comparison zone having a color corresponding to a predetermined pH level, and positioned and shaped for quick color comparison with the color of said indicator after indicator contact with vaginal moisture.

Another object is to provide a local comparison zone exhibiting a color which corresponds to a fixed standard, such as a predetermined pH level. That zone may be on the probe as for example in local and quick visual comparison proximity to the moisture responsive indicator.

A further object is to provide both the indicator and the color comparison zone to have substantially the same sizes and shapes, for enhancement of screening visual accuracy of color comparison, especially when the color of the zone (standard) is close to the color of the indicator as driven by vaginal moisture pH.

Another object is to locate the comparison zone and indicator mutually lengthwise of the probe for enhancement of "digital", side-by-side recognition of any deviation or differences between the colors of these elements indicating possible physical problems. The comparison zone "standard" color may be located on the surface of a plastic component, in substantially planer alignment with the plane of the indicator surface. Also, the indicator is preferably located closer to the probe tip than the "standard" zone, to enable or facilitate subsequent color comparison in side-by-side relation with a pH color chart. The amine test zone is typically at another side of the probe, and spaced from the pH test zone.

A yet further object is to provide a carrier for carrying the elements, and a pH color chart associated with the carrier.

An added object is to provide a device and method for quick testing to determine vaginal pH and also to test for bacterial vaginosis.

The method of quick screening for vaginal moisture pH level as it relates to a pre-selected pH level, includes the steps:

a) providing a manually manipulable element including a probe insertible into the vagina, b) providing at least one pH indicator on that element, the indicator characterized as producing a color which corresponds to pH level of vaginal moisture contacting the indicator, c) and providing a local comparison zone on the element having a color corresponding to a predetermined pH level, and positioned and shaped relative to the indicator for quick color comparison with the color of the indicator after indicator contact with vaginal moisture.

That method may include the steps of contacting the indicator with vaginal moisture, and then visually comparing the color of said "standard" zone with the color of the indicator.

In these regards, the color comparison zone standard may have a color associated with pH level of about 4.5, and which does not vary with changes in pH level of moisture in contact with the zone.

Yet another object is to provide a method for testing for vaginal pH and for vaginosis, using a single probe element that includes the steps:

a) providing at least one pH indicator on the probe element said indicator characterized as producing a color which corresponds to the pH level of vaginal moisture contacting the indicator, b) and locating a test site for vaginosis on the probe element in sufficiently spaced relation to the pH indicator so that vaginal moisture at the test site for vaginosis will not come into contact with the pH indicator, during normal use of said method. As will be seen the test site is a lengthwise extending strip that incorporates a hydroxide reactive with a vaginal bacterial produced amine. Also, the probe element may have opposite end portions adapted to be separately inserted into the vagina, the pH indicator located at one end portion and the test site for vaginosis located at the other end portion. A further object is to provide a probe element that has a mid-portion of a length adapted to be grasped by the user, for manipulating the probe to separately insert said opposite end portions into the vagina.

A yet further object is to provide a probe that has opposite sides, the pH indicator located at one of such sides, and the test site for vaginosis located at the other of such opposite sides.

These and other objects and advantages of the invention, as well as the details of an illustrative embodiment, will be more fully understood from the following specification and drawings, in which:

DRAWING DESCRIPTION

FIG. 1 is a top plan view of a probe and support incorporating the invention;

FIG. 2 is a bottom plan view of the FIG. 1 probe and support;

FIG. 3 is an edge view taken on lines 3-3 of FIG. 1;

FIG. 4 is a perspective view of the FIG. 1 probe and support;

FIG. 5 is a section taken on lines 5-5 of FIG. 1;

FIG. 6 is a section on line 6-6 of FIG. 1;

FIG. 7 is a view of the FIG. 1 probe received in a protective sheath;

FIG. 8 is a fragmentary view showing interlocking of the sheath and probe;

FIG. 9 is an enlarged view showing details of the sheath, with probe viewing window, and color comparison measurement zones, on the sheath; and also showing comparison of a color change of a test element with different colored zones on a sheath or other carrier;

FIG. 10 is a section taken on lines 10-10 of FIG. 9;

FIG. 17 shows use of the probe, as in a whiff test; and

FIG. 18 shows a kit embodying probe, ampule and calorimeter elements.

DETAILED DESCRIPTION

Figure 11:
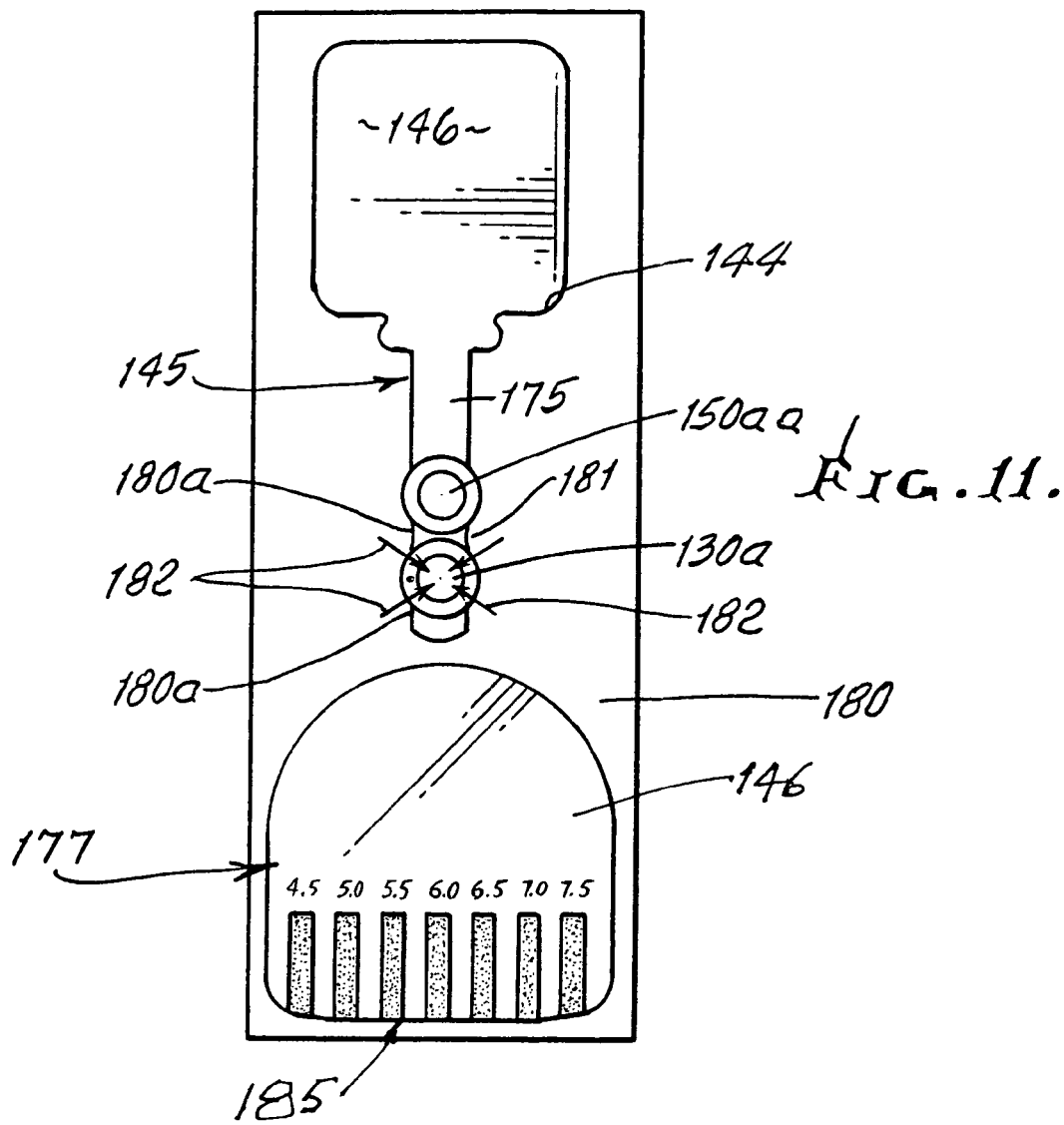
FIG. 11 is a side view of a preferred and modified apparatus.

Referring first to FIG. 1, it shows a device that includes:
a) a longitudinally elongated probe insertible into the vagina, for a test purpose,
b) a support operatively connected with the probe projecting away from the support,
c) the support including:
i) a manually manipulable handle,
ii) and an edge presented generally longitudinally for limiting probe insertion into the vagina.

As shown, the probe 10 of the apparatus 100 protrudes lengthwise from the support 12, which defines a handle 12*a* that can be easily gripped between the thumb 13 and forefinger 14 of the user, as seen in FIG. 3. The probe and support preferably have key-like configuration, as shown.

Forwardly or longitudinally presented edge 20 of the support limits insertion of the probe, as by engagement with the body 21, and dual edges may be provided as at 20*a* and 20*b*, at opposite lateral sides of the probe, for that purpose. The apparatus 100 may for example consist of plastic, metal or compressed fiber (example paper).

Surface irregularities may be provided on one laterally facing side of the support, and such irregularities are shown to extend longitudinally to be grasped by the thumb and prevent lateral slippage, relative to the user's thumb. The irregularities are shown in the form of protuberances 24 which are laterally spaced apart.

The probe and support, or handle may have the following dimensions for best results:
probe overall length "$l_1$" 1½ M to 2½ inches
probe width "$w_1$"=¼ to ½ inch
support width $w_2$=¾ to 1½ inch
thickness "t"=3/16 to 5/16 inch
overall length $l_2$ of probe and support=3¼ to 3¾ inches.
Preferably, $l_1 \cong 2$ inches
$w_1 \cong$ ⅜ inch
$w_2 \cong 1$¼ inch
$t \cong$ ¼ inch
$l_2 \cong 3$½ inch.

Also, the probe has an approximately flat, oval cross section, as seen in FIG. 6.

FIG. 1 also shows a test element or indicator 30 at the side of the probe, near its tip 31, to be pressed toward and against the vaginal wall. Element 30 typically comprises an indicator element, as for example one of the following:
i) a pH indicator
ii) an amine indicator
iii) a bacteria indicator
iv) sialidase indicator
v) prolidase indicator.

The pH indicator or detector typically takes the form of a Nitrazine® strip or other carrier element adhered to the side of the probe, as for example by double sided adhesive tape. After exposure of the strip to vaginal moisture, its changed color (according to pH level) is compared with the series 41 of bands on a sheath 42, as seen in FIG. 9. Each band has a different color corresponding to a pH level color to which the detector strip may change. See for example the indicated pH levels 4.5, 5.0, 5.5, 6.0, 6.5, 7.0 and 7.5 adjacent the color bands. The bands may be provided on a support strip 142 adhered to the outer surface of the sleeve or receptacle 42. See also FIG. 11 showing a manipulable element 145 including a probe 175 and handle 146 received in recesses 144 in a plastic carrier 180, with support strip 146 adhered to the carrier. A series of bands 185, like bands 41, is located on the strip 146. Paper strips providing such elements are known, and sold under the name HYDRION papers, by Micro Essential Laboratory Inc., Brooklyn, N.Y. 11210. The band for pH 4.5 is typically bright yellow; the band for pH 6.0 is olive in color; and the band for pH 7.5 is navy blue.

In FIG. 11 a standard comparison zone is provided on the probe, one example being a plastic part 150*aa* received in a recess in the probe in proximity to the pH sensitive indicator 130a. The outer surface of part 150aa has a color corresponding to a predetermined pH level, at or near neutral pH level, such as 4.5 for example, for quick visual color comparison with the color of the indicator, after indicator contact with vaginal moisture. When a Nitrazine® indicator is used, the surface of part 150aa can be sunflower yellow, to indicate a standard 4.5 pH. A corresponding part 150a is shown in FIGS. 1, 4 and 7.

In use, the user first visually compares the color of the indicator 130a (after exposure to vaginal moisture) and the standard zone (such as the surface of locality 150aa), and any difference in color indicates a possible problem. This consists of a screen test. The color, size, and location of standard zone 150 are such as to provide prominent visual color comparison of zone 150aa with the indicator. Next, the probe 175 and sleeve or receptacle 180 are relatively moved, to bring the detector indicator 130a (after its exposure to moisture and color change as referred to above) into lateral registration with the color comparison bands 185, enabling ready visual comparison of the color of the detector strip with the closest color of one of the bands, enabling a pH level determination. For this purpose, a window zone of the carrier sleeve adjacent the bands may be transparent to allow visual observation of the detector, through that zone, adjacent the bands.

In summary, the probe is inserted into the vagina to collect moisture and withdrawn, and the quick visual screen comparison is made, viewing the probe indictor and the standard comparison zone for quick detection of a possible problem, as for example need for estrogen. Thereafter, color comparison may be made with the colored bands, to more definitively determine moisture pH level. The probe is re-inserted into the elongated carrier receptacle 180.

The color changing reactant may consist, for example, of one or more of the following: Bromocresol Green, Bromocresol Purple, Nitrazine Yellow, Bromophenol Blue, and equivalents.

An optional procedure consists of obtaining a visual comparison of the color changed zone on the receiver 130a with a color? or different colors, or band color shades, as at 185, where one color band may indicate presence of putrecine; another color band may indicate presence of cadaverine; and a third band may have another color or color shade close to but different from the first two, and so indicating absence of putrecine or cadaverine, or other bacterial producing amine, i.e. an amine test when compared side-by-side with the color on the receiver 130a. Such amine indicates presence of pathogenic bacteria.

In FIG. 11, the indicator 130a and comparison zone 150a have substantially the same sizes and shapes, for enhancement of visual accuracy of color comparison. Also, the probe 145 has a substantially flat side 175, the indicator and comparison zones being exposed at that flat side. The local indicator and comparison zones are located in mutually edgewise convex proximity lengthwise of the probe, for rapid digital type color comparison readout (i.e. problem or no problem, per color visual differentiation). Both are substantially circular, and the exposed surfaces of each extend in substantially the same flat plane. Undulant edges 180a of the carrier and/or edges of 130a to 150a allow or facilitate relative travel of moisture along multiple paths 181 to reach the indicator 130a or zone 150a. See path arrows 182. The diameters of 130a and 150a may be between 3/16 and 3/8 inch, for optimum visual comparison effect. All of these contribute to enhancement of accurate, quick, viewing comparison to quickly detect color differences from a standard level. Carrier 180 receives the probe 145 and handle 146, and carries the pH color comparison chart 177.

Figure 12:
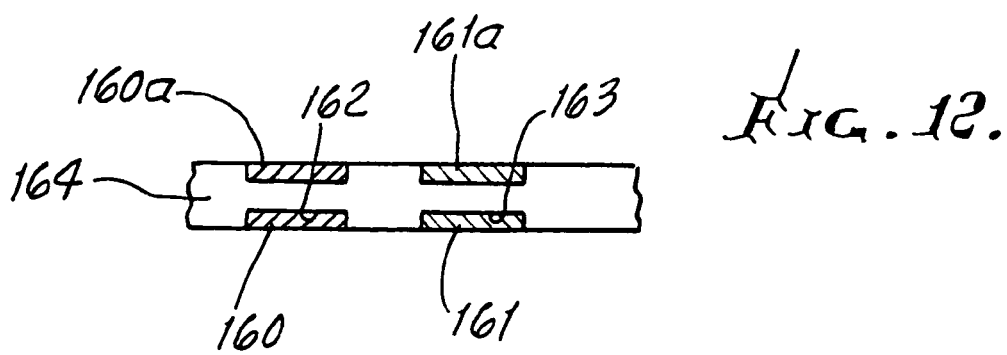
FIG. 12 is an enlarged view showing carrying on a probe of an indicator and comparison standard.

FIG. 12 shows reception of an indictor 160 and comparison zone plastic button 161, in recesses 162 and 163 in a probe 164, the outward facing surfaces of 160 and 161 being of generally the same size and shape and in the same plane for accuracy of comparison (equal illumination, light reflections, etc.).

Vaginal conditions related to pH are indicated as follows:

| | | |
|---|---|---|
| 1. Bacterial Infection | above | 4.5-6.5 |
| 2. Menopause | above | 4.5-6.5 |
| 3. SPROM | above | 4.5-7.5 |
| 4. Osteoporosis | above | 4.5-6.5 |

Additional indicators and standard comparison zones may be provided on the probe, as shown at 160a and 161a, in FIG. 12, for redundancy and color differentiation confirmation.

U.S. Pat. No. 6,406,441 is incorporated herein, by reference.

Figure 13:
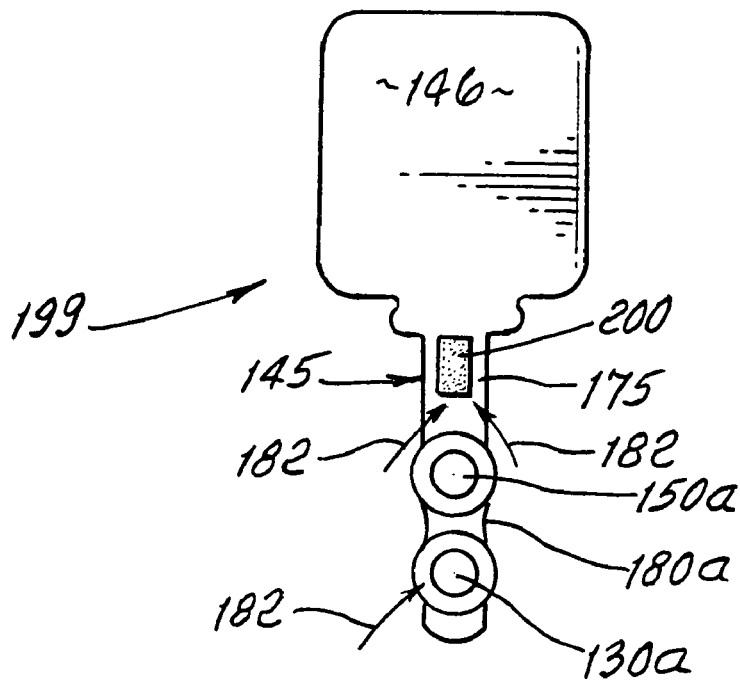
FIG. 13 is a view showing a vaginal probe with multiple test sites.

FIG. 13 shows a modification 199 in which elements the same as in FIG. 11 have the same identifying numerals. In addition, an elongated strip 200 is applied to the flat side 175 of the probe 145. Strip 200 includes, or carries, a thin layer of KOH, or other equivalent hydroxide reactive with an amine produced by vaginal bacteria, for use in testing for such an amine in the fluid sample from the vagina. See flow path arrow 182. When contacted with an amine in vaginal moisture the KOH reacts to produce a characteristic odor, which is a "fish" type odor, from which a doctor can diagnose the presence of amine in the test sample. Accordingly, the device 199 provides multiple test sites to enable quick multiple diagnostic tests for vaginal pH as may indicate estrogen deficiency as described, and for presence of amines (produced by vaginal bacteria) indicative of BV (i.e. bacterial vaginosis). Such amines include cadavarine and putrecine.

In FIGS. 11 and 13 it will be noted that the pH indicator and the local comparison zone are linearly aligned in the direction of the probe, being aligned on a line which extends between two lateral edges of the handle presented toward the test sites, the pH indicator and the comparison zone both having curved edges facing oppositely and convexly away from that line, and protruding at opposite sides of the probe.

Figure 14:
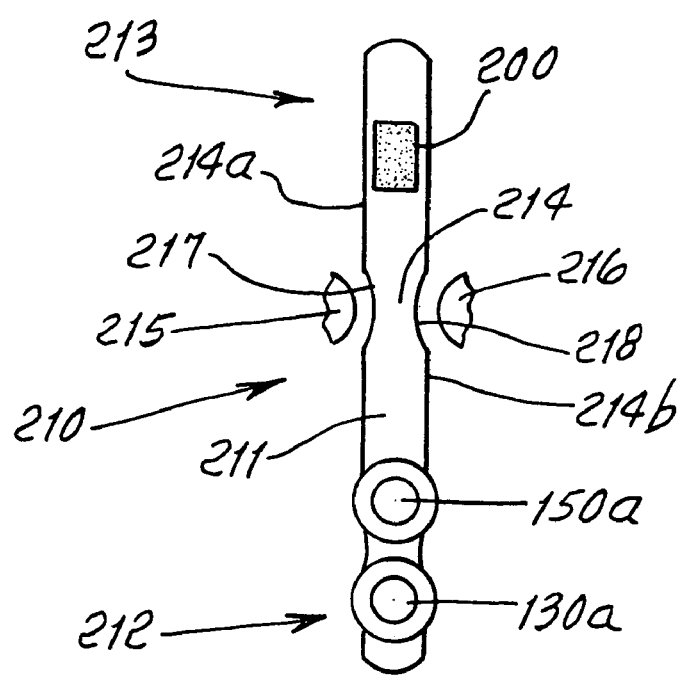
FIG. 14 shows another modification.

FIG. 14 shows a further modified device 210 which comprises an elongated thin stem 211 having test site zones 212 and 213 extending endwise oppositely of stem mid-portion 214. That mid-portion is adapted to be grasped as by the user's thumb 215 and first finger 216, during use of the device 210. There may be concave recesses 217, and 218 sunk in the edges 214a and 214b of stem mid-portion 214, for grasping and stem manipulation purposes. Test sites 130a and 150a at zone 212 are the same as provided in FIG. 13, i.e. have the same utility and relative placement.

Test site 200 has the same structure and utility as site 200 in FIG. 13; however, it is located at zone 213, remotely from sites 130a and 150a. In use the stem or stick is manipulated so that either zone 212 or zone 213 is first inserted into the vagina to receive vaginal moisture, and subsequently the stem is withdrawn and endwise removed so that the other of the zones 212 or 213 can then be separately inserted into the vagina to receive vaginal moisture and then withdrawn. This procedure avoids contact of moisture on site 200 with moisture on sites 130a and 150a, while still enabling rapid use and observation of all test sites 130a, 150a and 200. Such contact of moisture on site 200 with moisture on either or both of sites 130*a* and 150*a* could detrimentally change the pH at those latter sites due to the pH of the hydroxide containing moisture at site 200. As an alternative, the device of FIG. 13 could be modified to place site 200 at the opposite side of the stem 175, so that moisture on site 200 would be unlikely to be displaced as by smearing to contact moisture at sites 130*a* and 150*a*, at the opposite sides of the stem.

A protective film may be applied to cover site 200 until use, as for example by application to KOH or other hydroxide at the site of vaginal discharge, i.e applied for example by a Q-tip.

Figure 15:
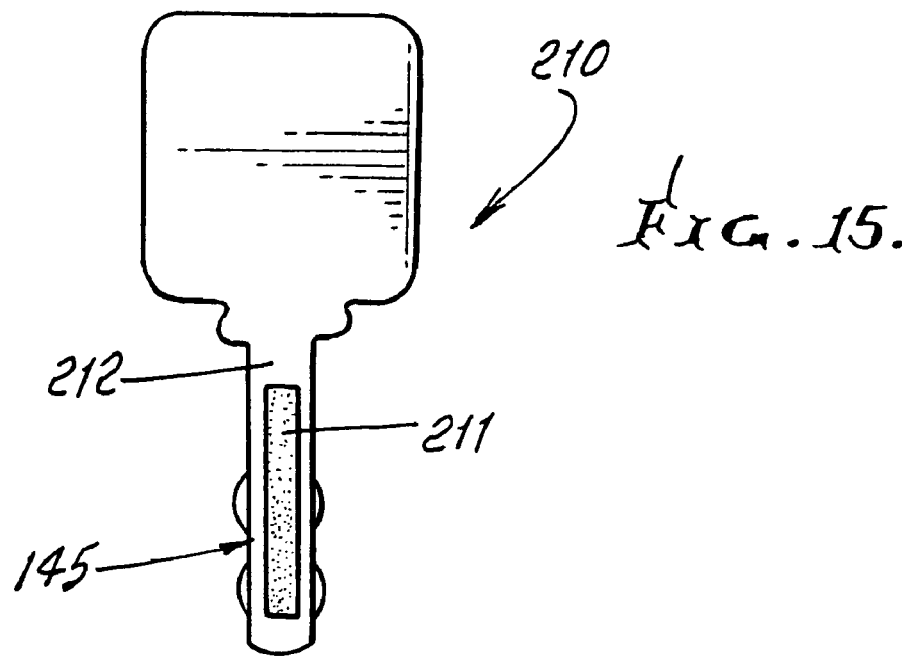
FIG. 15 shows a further modification on one side of a probe.
Figure 16:
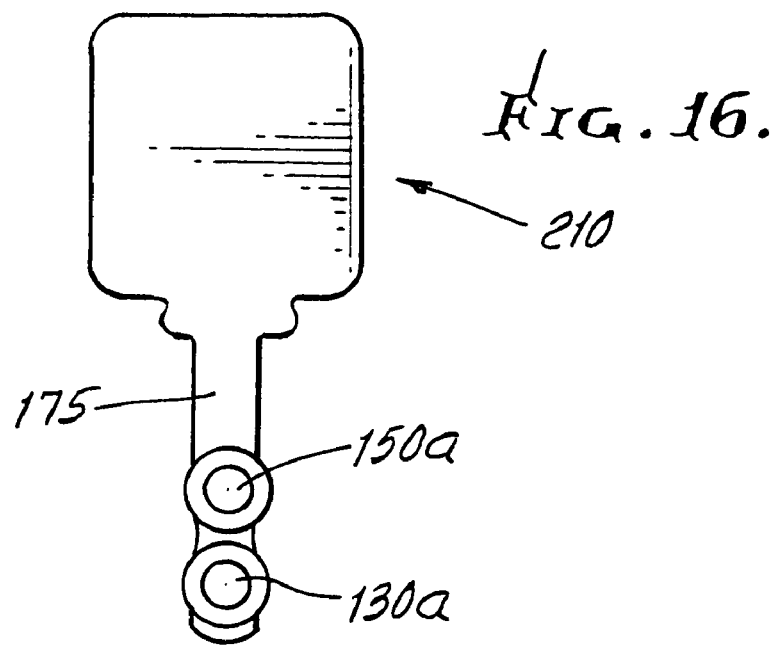
FIG. 16 shows the opposite side of the probe as seen in FIG. 15.

FIGS. 15 and 16 show a preferred modification 210 in which elements the same as in FIG. 11 have the same identifying numerals. In addition an elongated absorbent strip 211 is attached to the flat opposite side 212 of the probe 145, where side 212 is opposite side 175. In use, sides 175 and 212 are exposed to moisture in the vagina, and the probe is then removed. Strip 211 constitutes a test site for production of amine or amines, such as cadaverine and putrecine. An hydroxide is then applied to the test site at moistened strip 211, externally of the vagina so contact of hydroxide with the vagina is avoided. See drops 214 of liquid hydroxide in FIG. 17, applied to strip 211, the amount of applied hydroxide being easily controllable, as by manipulation of an ampule 216.

As referred to above, when contacted with an amine in vaginal moisture, the hydroxide reacts to produce a characteristic odor, which is a "fish" type odor, from which a user 219 can detect (as seen at 220 in FIG. 17) the presence of amines in the test at the test site.

Accordingly, the device 210 provides multiple test sites to enable quick multiple diagnostic tests for vaginal pH as may indicate estrogen deficiency as described, and for presence of amine (produced by vaginal bacteria) indicative of bacterial vaginosis.

By avoiding inclusion of hydroxide on the probe at the time of insertion into the vagina, undesirable application or mixing of hydroxide with the pH test sites seen in FIG. 16 is avoided, whereby erroneous readings of pH are avoided. Strip 211 can thus be located at the direct opposite side of the probe from the pH indicators 130*a* and 150*a*, without risk of hydroxide contamination of those sites. Usable hydroxides include: KOH, milk of magnesia, baking soda and sea water, as well as others. The strip 211 may consist of a "Super Absorbent Polymer" such as "Waste Lock", from M2 Polymer, or the highly moisture absorbent "Lyocell Fiber" referenced in "Medical Textiles", June 2003, at page 3, as well as others, such as filter paper.

FIG. 18 shows a kit 230 including a carrier tray 231; probe 210 on the tray; and hydroxide ampules 216 on the tray; and a pH color comparison chart 177 on the tray. That type chart use also referenced in FIG. 11. Elements of the kit are used as described in FIGS. 15-17, after removal from the tray.

In the above, the word "hydroxide" is intended to include, within its scope, alkaline substances, that may for example be flowable.

I claim:

1. The method of quickly screening for vaginal moisture conditions, that includes:
    a) providing a manually manipulable generally key shaped element including a probe insertible into the vagina,
    b) providing one or more pH indicating first test site or sites on one end portion of the probe,
    c) providing a vaginosis test site on a different portion of the probe, near said one end portion,
    d) manipulating the probe to transfer vaginal moisture to said sites, simultaneously,
    e) and, thereafter, externally of the vagina, applying an hydroxide in liquid form to the vaginosis test site, to come in contact with moisture at said vaginosis test site,
    f) and detecting presence of an amine or amines produced at said vaginosis site,
    g) wherein said pH test site or sites include
        i) a pH indicator characterized as producing a color which corresponds to pH level of vaginal moisture contacting the indicator,
        ii) a local comparison zone having a color corresponding to a predetermined pH level, and positioned and shaped for quick color comparison with the color of said indicator after indicator contact with vaginal moisture,
        iii) said local comparison zone being substantially adjacent said indicator,
    h) and wherein said element is provided to include an enlarged substantially flat handle from which the probe projects longitudinally to be gripped between the user's thumb and forefinger, the handle having two laterally shaped edges presented toward said test site or sites and spaced generally longitudinally therefrom to limit probe longitudinal insertion into the vagina, said pH indicator and said local comparison zone being aligned on a line which extends between said two edges, and both having curved edges facing oppositely and convexly away from said line, and protruding at opposite edges of said probe.

2. The method of claim 1 including
    g) withdrawing the probe from the vagina between said steps d) and e), and
    h) observing the coloration of said pH indication site as an indication of pH level.

3. The method of claim 1 wherein the probe has opposite sides, said one portion of the probe located at one of said sides, and said different portion of the probe located at another of said opposite sides.

4. The method of claim 1 wherein said hydroxide is selected from the group:
    i) KOH,
    ii) milk of magnesia,
    iii) sea water,
    iv) baking soda, or mixture thereof with water.

5. The method of claim 1 wherein said detecting step includes a nasal whiff test.

6. The method of claim 1 wherein said probe has opposite sides, and said vaginosis test site is at one of said opposite sides, and said first site or sites is at another of said opposite sides.

7. The method of claim 6 wherein said vaginosis site is elongated along the probe.

8. The method of claim 1 including providing a carrier for said hydroxide, and effecting said application of the hydroxide to the vaginosis test site after said moisture transfer thereto.

9. The method of claim 8 including preliminarily providing a support for said probe and for said hydroxide carrier, assembled as a test kit.

10. The method of claim 8 wherein said hydroxide carrier is provided in the form of an ampule.

11. The method of claim 10 including preliminarily providing a support for said probe and for said ampule, assembled as a test kit.

12. Apparatus for quickly screening for vaginal moisture conditions, comprising:

a) a manually manipulable element including a probe insertible into the vagina,
b) two similar test sites on one end portion of the probe, said test sites relatively closely spaced apart mutually convexly edgewise at one side of the probe, one site being a pH indicator and the other a local comparison zone,
c) a vaginosis test site on another portion of the probe, near said one end portion,
d) the probe being manipulable to transfer vaginal moisture to said sites,
e) an hydroxide carrier to dispense an hydroxide in liquid form to the vaginosis test site, externally of the vagina to come in contact with moisture at said vaginosis test site,
f) whereby an amine or amines produced at the vaginosis site may be efficiently detected,
g) said element provided to include an enlarged substantially flat handle from which the probe projects longitudinally to be gripped between the user's thumb and forefinger, the handle having two laterally shaped edges presented toward said test site or sites and spaced generally longitudinally therefrom to limit probe longitudinal insertion into the vagina, said pH indicator and said local comparison zone being aligned on a line which extends between said two edges, and both having curved edges facing oppositely and convexly away from said line, and protruding at opposite edges of said probe.

13. The apparatus of claim 12 wherein said similar test sites undulate similarly at opposite edges of the probe.

14. The combination apparatus of claim 13 wherein said vaginosis test site is in the form of a strip elongated in the probe length direction, toward said local comparison zone.

15. The method of quickly screening for vaginal moisture conditions that includes:
    a) providing the apparatus as defined in claim 12,
    b) manipulating the probe to simultaneously transfer vaginal moisture to said test sites,
    c) and, thereafter, externally of the vagina, applying said hydroxide in liquid form to said vaginosis test site to come in contact with moisture at said vaginosis test site,
    d) and detecting presence of an amine or amines produced at said vaginosis test site.

* * * * *